United States Patent [19]

Kasamatsu et al.

[11] Patent Number: 4,518,594
[45] Date of Patent: May 21, 1985

[54] USE OF TRIFLUOROMETHANESULFONANILIDES

[75] Inventors: Kiyoshi Kasamatsu, Toyonaka; Hiroyuki Konishi, Sakai, both of Japan

[73] Assignee: Sumitomo Chemical Company, Limited, Osaka, Japan

[21] Appl. No.: 530,265

[22] Filed: Sep. 8, 1983

[51] Int. Cl.$^3$ .............................................. A01N 51/00
[52] U.S. Cl. ...................................................... 514/155
[58] Field of Search .......................................... 424/228

[56] References Cited

U.S. PATENT DOCUMENTS 3,639,474  2/1972  Harrington .......................... 564/97
3,920,444  11/1975  Harrington et al. ................. 71/72

FOREIGN PATENT DOCUMENTS 0072253  2/1983  European Pat. Off. .

OTHER PUBLICATIONS

Chemical Abstracts, vol. 55, (1955), 14379d, Muth, F.

*Primary Examiner*—Leonard Schenkman
*Assistant Examiner*—Joseph A. Lipovsky
*Attorney, Agent, or Firm*—Birch, Stewart, Kolasch & Birch

[57] ABSTRACT

An insecticidal composition which comprises as an active ingredient a compound of the formula:

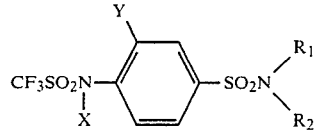

wherein X is a hydrogen atom or an acyl group, Y is a hydrogen atom, a lower alkyl group or a halogen atom and $R_1$ and $R_2$, which may be the same or different, are each a hydrogen atom, a lower alkyl group, a cyclo(-lower)alkyl group, a lower alkenyl group, a lower alkynyl group, a lower alkoxy group or an acyl group, provided that $R_1$ and $R_2$ are not simultaneously a hydrogen atom or an acyl group.

6 Claims, No Drawings

USE OF TRIFLUOROMETHANESULFONANILIDES

The present invention relates to a new use of trifluoromethanesulfonanilides.

The said trifluoromethanesulfonanilides are representable by the formula:

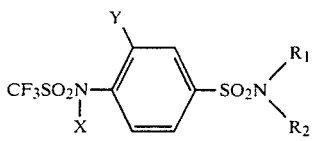
(I)

wherein X is a hydrogen atom or an acyl group, Y is a hydrogen atom, a lower alkyl group or a halogen atom and $R_1$ and $R_2$, which may be the same or different, are each a hydrogen atom, a lower alkyl group, a cyclo(lower)alkyl group, a lower alkenyl group, a lower alkynyl group, a lower alkoxy group or an acyl group, provided that $R_1$ and $R_2$ are not simultaneously a hydrogen atom or an acyl group.

Particularly preferred are those of the formula (I) wherein X is a hydrogen atom or an acyl group, Y is a fluorine atom or a chlorine atom and $R_1$ is a hydrogen atom, a methyl group or an ethyl group and $R_2$ is a methyl group, an ethyl group or a 2-propynyl group.

In the above significances, the term "lower" is intended to mean any group having not more than 8 carbon atoms. Preferably, lower alkyl is alkyl having 1 to 5 carbon atoms, lower alkenyl is alkenyl having 2 to 5 carbon atoms and lower alkynyl is alkynyl having 2 to 5 carbon atoms. Cyclo(lower)alkyl is preferred to have 3 to 6 carbon atoms, and lower alkoxy is favored to have 1 to 5 carbon atoms. The term "acyl" represents preferably lower alkanoyl, lower alkenoyl, benzoyl, etc. Examples of the halogen atom includes fluorine, chlorine, etc.

It is known that certain kinds of trifluoromethanesulfonanilides are effective as herbicides. For instance, the herbicidal use of 2-methyl-4-(N-methylsulfamoyl)trifluoromethanesulfonanilide and 3-(N,N-dimethylsulfamoyl)trifluoromethanesulfonanilide (U.S. Pat. No. 3,920,444) is known. However, their insecticidal activity has never been known.

It has now been found that the trifluoromethanesulfonanilides (I) exert a remarkable insecticidal activity on a variety of insects belonging to the groups Hemiptera, Lepidoptera, Coleoptera, Diptera, Acarina, etc. in agricultural fields (e.g. paddy field, crop field), orchards, forest lands, granaries, stored products, sanitary facilities, etc. Specific examples of the insects are as follows:

1. Hemiptera: brown planthopper (*Nilaparvata lugens*), smaller brown planthopper (*Laodelphax striatellus*), green rice leafhopper (*Nephotettix cincticeps*), green peach aphid (*Myzus persicae*), cotton aphid (*Aphis gossypii*), etc.
2. Lepidoptera: rice stem borer (*Chilo suppressalis*), tobacco cutworm (*Spodoptera litura*), diamond back moth (*Plutella xylostella*), egger (*Dendrolimus spectabilis*), cotton leaf worm (*Spodoptera littoralis*), etc.
3. Coleoptera: varied carpet beetle (*Anthrenus verbasci*), tobacco beetle (*Lasioderma serricorne*), powder-post beetle (*Lyctus brunneus*), etc.
4. Diptera: yellow fever mosquito (*Aedes aegypti*), malaria mosquito (*Anopheles stephansi*), common mosquito (*Culex pipiens pallens*), housefly (*Musca domestica*), etc.
5. Acarina: carmine spider mite (*Tetranychus cinnabarinus*), two-spotted spider mite (*Tetranychus urticae*), citrus red mite (*Panonychus citri*), cattle tick (*Boophilus microplus*), etc.

Accordingly, the trifluoromethanesulfonanilides (I) are useful as insecticides against a wide variety of harmful insects as above mentioned.

The trifluoromethanesulfonanilides (I) are known and may be prepared in such conventional manners as disclosed in U.S. Pat. No. 3,920,444 and EP No. 0072253A.

Specific examples of the trifluoromethanesulfonanilides (I) are shown in Table 1.

TABLE 1

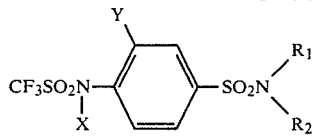

| Compound No. | X | Y | $R_1$ | $R_2$ | Physical property |
|---|---|---|---|---|---|
| 1 | H | H | H | $CH_3$ | M.P. 156–157° C. |
| 2 | H | H | $CH_3$ | $CH_3$ | M.P. 172.5–173.5° C. |
| 3 | H | H | $C_2H_5$ | $C_2H_5$ | $n_D^{18}$ 1.5052 |
| 4 | H | $CH_3$ | H | $CH_3$ | M.P. 132–132.5° C. |
| 5 | H | $CH_3$ | $CH_3$ | $CH_3$ | M.P. 161–161.5° C. |
| 6 | H | $CH_3$ | $CH_3$ | $C_3H_7(n)$ | M.P. 112–113° C. |
| 7 | H | $CH_3$ | $CH_3$ | $-CH_2C\equiv CH$ | M.P. 111–112° C. |
| 8 | H | $CH_3$ | H | $OCH_3$ | M.P. 130–131° C. |
| 9 | H | $CH_3$ | $C_2H_5$ | $C_2H_5$ | M.P. 128–128.5° C. |
| 10 | H | $CH_3$ | $C_2H_5$ | $C_3H_7(n)$ | M.P. 104.5–106.5° C. |
| 11 | H | $CH_3$ | H | $C_3H_7(n)$ | M.P. 75.5–79° C. |
| 12 | H | $CH_3$ | $C_3H_7(n)$ | $C_3H_7(n)$ | M.P. 116.5–117.5° C. |
| 13 | H | $CH_3$ | H | $C_3H_7(iso)$ | M.P. 124.5–125° C. |
| 14 | H | $CH_3$ | $C_2H_5$ | $C_3H_7(iso)$ | $n_D^{19.8}$ 1.4959 |
| 15 | H | $CH_3$ | H | ▽ | M.P. 126–127° C. |
| 16 | H | $CH_3$ | H | $-CH_2CH=CH_2$ | M.P. 101–103° C. |

TABLE 1-continued $$CF_3SO_2N(X)-C_6H_3(Y)-SO_2N(R_1)(R_2)$$

| Compound No. | X | Y | R₁ | R₂ | Physical property |
|---|---|---|---|---|---|
| 17 | H | CH₃ | H | —CH₂≡CH | M.P. 106–107° C. |
| 18 | H | CH₃ | H | cyclobutyl | M.P. 120.5–122° C. |
| 19 | H | CH₃ | H | —C(CH₃)₂—C≡CH | M.P. 124.5–125.5° C. |
| 20 | H | C₂H₅ | CH₃ | CH₃ | M.P. 122–123° C. |
| 21 | H | C₂H₅ | H | C₂H₅ | M.P. 118–119.5° C. |
| 22 | H | C₂H₅ | C₂H₅ | C₂H₅ | $n_D^{18}$ 1.4928 |
| 23 | H | C₂H₅ | H | C₃H₇(iso) | M.P. 83.5–85° C. |
| 24 | H | C₂H₅ | H | C₄H₉(t) | M.P. 111.5–113.5° C. |
| 25 | H | Cl | H | CH₃ | M.P. 107–111° C. |
| 26 | H | Cl | CH₃ | CH₃ | M.P. 158–159° C. |
| 27 | H | Cl | H | C₂H₅ | M.P. 111.5–113° C. |
| 28 | H | Cl | C₂H₅ | C₂H₅ | M.P. 110–114° C. |
| 29 | H | Cl | H | C₄H₉(t) | M.P. 123–127.5° C. |
| 30 | H | Cl | H | —CH₂CH=CH₂ | M.P. 94–95° C. |
| 31 | H | Cl | H | —CH₂C≡CH | M.P. 76.5–82° C. |
| 32 | H | F | H | CH₃ | M.P. 118–120° C. |
| 33 | H | F | H | C₂H₅ | M.P. 103–104° C. |
| 34 | H | F | C₂H₅ | C₂H₅ | M.P. 76–77° C. |
| 35 | H | F | H | C₃H₇(n) | M.P. 75–76° C. |
| 36 | H | F | CH₃ | CH₃ | M.P. 163.5–164° C. |
| 37 | H | F | H | —CH₂CH=CH₂ | M.P. 95.5–96° C. |
| 38 | H | F | H | —CH₂C≡CH | M.P. 126.5–127.5° C. |
| 39 | H | F | CH₃ | —CH₂C≡CH | M.P. 87–90° C. |
| 40 | —C(=O)CH₃ | CH₃ | CH₃ | CH₃ | M.P. 148–148.5° C. |
| 41 | —C(=O)CH₃ | CH₃ | —C(=O)CH₃ | CH₃ | M.P. 130–131.5° C. |
| 42 | —C(=O)CH₃ | CH₃ | H | C₄H₉(t) | M.P. 94–97.5° C. |
| 43 | —C(=O)C₂H₅ | CH₃ | CH₃ | CH₃ | M.P. 130.5–131.5° C. |
| 44 | —C(=O)C₂H₅ | CH₃ | H | C₄H₉(t) | M.P. 114.5–115° C. |
| 45 | —C(=O)C₃H₇(n) | CH₃ | CH₃ | CH₃ | M.P. 98–98.5° C. |
| 46 | —C(=O)C₃H₇(n) | CH₃ | H | C₄H₉(t) | M.P. 87.5–88.5° C. |
| 47 | —C(=O)C₃H₇(iso) | CH₃ | CH₃ | CH₃ | M.P. 101–102° C. |
| 48 | —C(=O)CH=CHCH₃ | CH₃ | CH₃ | CH₃ | M.P. 110.5–114° C. |

TABLE 1-continued

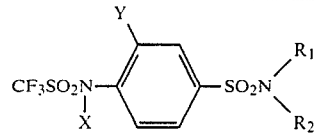

| Compound No. | X | Y | $R_1$ | $R_2$ | Physical property |
| --- | --- | --- | --- | --- | --- |
| 49 | H | $CH_3$ | $CH_3$ | $OCH_3$ | M.P. 114.5-115.5° C. |

On the practical application as an insecticide, the trifluoromethanesulfonanilides (I) are used in the form of appropriate compositions such as oily preparations, emulsifiable concentrates, wettable powders, granules, dusts and aerosols. The content of the trifluoromethanesulfonanilide (I) in such composition may be from about 0.1 to 99.9% by weight, preferably from about 1 to 80% by weight.

The composition can be formulated in a per se conventional manner by mixing at least one of the trifluoromethanesulfonanilides (I) with an appropriate solid, liquid or gaseous carrier(s) or diluent(s) with or without an appropriate auxiliary agent(s) such as surfactants, adherents, dispersants and stabilizers for improving the dispersibility and other properties of the active ingredient.

Examples of the solid carriers or diluents are clays (e.g. kaolin, diatomaceous earth, synthetic hydrated silica, fubasami clay, bentonite, terra abla), talcs and other inorganic materials (e.g. sericite, sulfur powder, active carbon, calcium carbonate, hydrated silica) in fine powders or powdery form. Chemical fertilizers (e.g. ammonium sulfate, ammonium phosphate, ammonium nitrate, urea, ammonium chloride) may be also used as the solid carriers or diluents.

Examples of the liquid carriers or diluents are water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexanone, kerosene, petroleum), esters, nitriles, ethers, acid amides (e.g. methylformamide, dimethylacetamide), halogenated hydrocarbons (e.g. dichloroethane, trichloroethylene, carbon tetrachloride), etc.

As the gaseous carriers or diluents, there may be exemplified freon gas, butane gas, carbon dioxide gas, etc.

Examples of the surfactants are alkylsulfates, alkylsulfonates, alkylarylsulfonates, alkylaryl ethers and their condensates with polyoxyethylene, polyethylene glycol ethers, polyhydric alcohol esters, glycitol derivatives, etc. Examples of the adherents and dispersants may include casein, gelatin, polysaccharides (e.g. starch powder, gum arabic, cellulose derivative, alginic acid), ligninsulfonate, bentonite, monosaccharides, synthetic watersoluble high polymer (e.g. polyvinyl alcohol, polyvinyl pyrrolidone, polyacrylic acid), etc. As the stabilizers, there may be used PAP (isopropyl acid phosphates), BHT (2,6-di-t-butyl-4-methylphenol), BHA (mixture of 2-t-butyl-4-methoxyphenol and 3-t-butyl-4-methoxyphenol), natural vegetable oil, mineral oil, the above mentioned surfactants, fatty acids (e.g. oleic acid, linolic acid, linolenic acid) and their esters, etc.

The trifluoromethanesulfonanilides (I) thus formulated into an appropriate composition may be applied as such or in dilution with water in a conventional application mode such as spraying, smoking, soil treatment, soil surface treatment or in combination with animal feed. The compounds may also be used together with or in admixture with other insecticides, acaricides, namatocides, fungicides, seed disinfectants, fertilizers or, soil improvers.

Some practical embodiments of the insecticidal composition according to the invention are illustratively shown in the following examples wherein part(s) and % are by weight.

EXAMPLE 1

Each of Compound Nos. 1 to 49 (50 parts) and an emulsifier ("Sorpol 2495 G"; a mixture of polyoxyethylene alkylaryl ether sulfate and alkylarylsulfonate) (5 parts) are mixed well, and the resultant mixture is admixed with diatomaceous earth (300 mesh) (45 parts) in a pulverizer to make a wettable powder.

EXAMPLE 2

Each of Compound Nos. 1 to 49 (10 parts) and an emulsifier ("Sorpol 5029 O"; sodium laurylsulfate) (5 parts) are mixed well, and the resultant mixture is admixed with diatomaceous earth (300 mesh) (85 parts) in a pulverizer to make a wettable powder.

EXAMPLE 3

Each of Compound Nos. 1 to 49 (10 parts), an emulsifier ("Sorpol 3005 X"; a mixture of polyoxyethylenestyrylphenyl ether and alkylarylsulfate) (10 parts), dimethylformamide (40 parts) and xylene (40 parts) are mixed well to make an emulsifiable concentrate.

EXAMPLE 4

Each of Compound Nos. 1 to 49 (0.1 part) and xylene (1 part) were dissolved in kerosene (98.9 parts) to obtain an oily preparation.

EXAMPLE 5

Each of Compound Nos. 1 to 49 (1 part) is dissolved in an appropriate amount of acetone, and talc (300 mesh) (99 parts) is added thereto. The resultant mixture is stirred and mixed well, followed by evaporation of acetone to obtan dusts.

The dosage rate of the trifluoromethanesulfonanilide (I) as the active ingredient may be from 1 to 1000 grams, preferably from 5 to 200 grams per are, and in the insecticidal composition the content thereof may be from 0.005 to 30% by weight, although these parameters may vary depending upon the season, the places of application, the mode, the kind of insects, the degree of damage, and so forth.

The following Examples show some typical test data indicating the excellent insecticidal activity of the trifluoromethanesulfonanilides (I) wherein the determination is made with three replications unless otherwise indicated. The compounds used for comparison are as follows:

| Compound No. | Chemical structure | Remarks |
|---|---|---|
| A | CH₃O–P(=S)(OCH₃)–O–C₆H₃(CH₃)(SCH₃) | Commercially available insecticide "phenthion" |
| B | C₂H₅O–P(=S)(OC₂H₅)–O–C(=N–C(iso-C₃H₇)=N)–CH₃ (pyrimidine ring) | Commercially available insecticide "diazinon" |
| C | 1-naphthyl-O-C(=O)-NHCH₃ | Commercially available insecticide "carbaryl" |

TEST EXAMPLE 1

Each of Compound Nos. 1 to 49 formulated into an emulsifiable concentrate according to Example 3 was diluted with water to prepare four designed concentrations. Separately, an artificial diet (13 g) comprising powdered kidney beans and powdered soybean leaf for tobacco cutworm was supplied in plastic cups (250 ml volume) and coated with the above prepared concentrations. Larvae of tobacco cutworm of the fourth instar (10 insects per cup) were released therein. Six days thereafter, the numbers of the survived insects were counted, whereby LC₅₀ (ppm) was calculated from the mortality of the insect in relation to the designed concentration. The results are shown in Table 2.

TABLE 2

| Compound No. | $LC_{50}$ (ppm) |
|---|---|
| 1 | 27 |
| 2 | 15–50 |
| 3 | ≈15 |
| 4 | 22 |
| 5 | 37 |
| 6 | 78 |
| 7 | 28 |
| 8 | 76 |
| 9 | ≈15 |
| 10 | 60 |
| 11 | 50 |
| 12 | 150 |
| 13 | 15–50 |
| 14 | 68 |
| 15 | 92 |
| 16 | 27 |
| 17 | 15–50 |
| 18 | 110 |
| 19 | 34 |
| 20 | ≦15 |
| 21 | 29 |
| 22 | 15 |
| 23 | 32 |
| 24 | 53 |
| 25 | ≦15 |
| 26 | 6.6 |
| 27 | 9.0 |
| 28 | ≦15 |
| 29 | 35 |
| 30 | ≈15 |
| 31 | ≈15 |
| 32 | ≦15 |
| 33 | 5–15 |
| 34 | ≦15 |
| 35 | 18 |
| 36 | ≦15 |
| 37 | ≦15 |
| 38 | 5 |
| 39 | ≈15 |
| 40 | 13 |
| 41 | 35 |
| 42 | 56 |
| 43 | 40 |
| 44 | 68 |
| 45 | 25 |
| 46 | 70 |
| 47 | 30 |
| 48 | 28 |
| 49 | 50–100 |
| A | 350 |
| B | 87 |
| C | ≧500 |

TEST EXAMPLE 2

Each of Compound Nos. 29, 33, 34, 35, 37, 38, 39, 41, 42, 43, 44 and 48 formulated into a wettable powder according to Example 1 was diluted with water to make a 50 ppm concentration in terms of the active ingredient. The thus prepared dilution was thoroughly sprayed to cabbages planted in pots (diameter, 12 cm) and allowed to dry. Larvae of tobacco cutworm of the fourth instar (5 insects) were released to each pot, which was then laid in a cylindrical cage (diameter, 18 cm, height, 30 cm) and allowed to stand in a room. Six days thereafter, the numbers of survived insects were counted, whereby the mortality was calculated. The results are shown in Table 3.

TABLE 3

| Compound No. | Mortality (%) |
|---|---|
| 29 | 80 |
| 33 | 100 |
| 34 | 100 |
| 35 | 100 |
| 37 | 100 |
| 38 | 100 |
| 39 | 100 |
| 41 | 100 |
| 42 | 47 |
| 43 | 93 |
| 44 | 33 |
| 48 | 87 |
| A | 7 |
| Non-treatment | 0 |

TEST EXAMPLE 3

Each of Compound Nos. 35, 38 and 40 formulated into an emulsifiable concentrate according to Example 3 was diluted with water to make a 100 ppm concentration in terms of the active ingredient, and to this dilution there was added "New Gramine" (a mixture of polyoxyethylenedodecyl ether, polyoxyethylenealkylaryl ether and ligninsulfonate) so as to make a 3000 fold dilution. Cabbage leaves at 2 months after sowing were dipped in the dilution and, after being allowed to dry, laid in plastic cups (diameter, 9 cm; height, 4 cm) together with larvae of cotton leaf worm of the second instar (10 worms per cup). The cups were then allowed to stand in a room for 3 days, and the numbers of survived insects were counted, whereby the mortality was calculated. The results are shown in Table 4.

TABLE 4

| Compound No. | Mortality (%) |
|---|---|
| 35 | 100 |
| 38 | 100 |
| 40 | 100 |
| Non-treatment | 7 |

What is claimed is:

1. A method for exterminating insects which comprises applying an insecticidally effective amount of a compound of the formula:

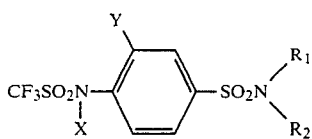

wherein X is a hydrogen atom or a lower alkanoyl, lower alkenoyl or benzoyl group, Y is a hydrogen atom, a lower alkyl group or a halogen atom and $R_1$ and $R_2$, which may be same or different, are each a hydrogen atom, a lower alkyl group, a cyclo(lower)alkyl group, a lower alkenyl group, a lower alkynyl group, a lower alkoxy group or an acyl group selected from the group consisting of a lower alkanoyl, a lower alkenoyl and a benzoyl group, provided that $R_1$ and $R_2$ are not simultaneously a hydrogen atom or an acyl group, to said insects.

2. The method according to claim 1, wherein the insects belong to Lepidoptera.

3. A method according to claim 1, wherein X is a hydrogen atom, Y is a chlorine atom and $R_1$ and $R_2$ are each a methyl group.

4. A method according to claim 1, wherein X is a hydrogen atom, Y is a fluorine atom, $R_1$ is a hydrogen atom and $R_2$ is a 2-propynyl group.

5. A method according to claim 1, wherein X is a hydrogen atom, Y is a fluorine atom, and $R_1$ and $R_2$ are each an ethyl group.

6. A method according to claim 1, wherein X is a hydrogen atom, Y is a fluorine atom, $R_1$ is a methyl group and $R_2$ is a 2-propenyl group.

* * * * *